US00PP14526P29

(12) United States Plant Patent
DeSilva

(10) Patent No.: US PP14,526 P2
(45) Date of Patent: Feb. 10, 2004

(54) POINSETTIA PLANT NAMED 'TED'S RED'

(50) Latin Name: *Euphorbia pulcherrima*
Varietal Denomination: Ted's Red

(75) Inventor: Heidi Tietz DeSilva, Waterloo, IA (US)

(73) Assignee: Petersen & Tietz Florists + Greenhouses, Inc., Waterloo, IA (US)

( * ) Notice: Subject to any disclaimer, the term of this patent is extended or adjusted under 35 U.S.C. 154(b) by 0 days.

(21) Appl. No.: 10/324,934

(22) Filed: Dec. 20, 2002

(51) Int. Cl.[7] ..... A01H 5/00

(52) U.S. Cl. ..... Plt./307

(58) Field of Search ..... Plt./307

*Primary Examiner*—Bruce R. Campell
*Assistant Examiner*—June Hwu
(74) *Attorney, Agent, or Firm*—C. A. Whealy

(57) ABSTRACT

A new and distinct cultivar of Poinsettia plant named 'Ted's Red', characterized by its uniform, compact, upright and mounded plant habit; freely branching growth habit; narrow branching angle that reduces stem breakage; inflorescences with upright red-colored flower bracts; relatively late flowering; and excellent post-production longevity; flower bracts resist fading.

1 Drawing Sheet

Botanical classification/cultivar designation: *Euphorbia pulcherrima* Willd. cultivar Ted's Red.

BACKGROUND OF THE INVENTION

The present Invention relates to a new and distinct cultivar of Poinsettia plant, botanically known as *Euphorbia pulcherrima* Willd., and hereinafter referred to by the cultivar name 'Ted's Red'.

The new Poinsettia is a naturally-occurring branch mutation of the *Euphorbia pulcherrima* Willd. cultivar Red Sails, disclosed in U.S. Plant Pat. No. 6,980. The new Poinsettia was discovered and selected by the Inventor from within a population of flowering plants of the cultivar Red Sails in July, 1998, in a controlled environment in Waterloo, Iowa. The selection of this plant was based on the upright orientation of its red-colored flower bracts.

Asexual reproduction of the new Poinsettia by terminal cuttings propagated in a controlled environment in Waterloo, Iowa, since July, 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Ted's Red'. These characteristics in combination distinguish 'Ted's Red' as a new and distinct cultivar:

1. Uniform, compact, upright and mounded plant habit.
2. Freely branching growth habit.
3. Narrow branching angle that reduces stem breakage.
4. Inflorescences with upright red-colored flower bracts.
5. Relatively late flowering; natural season flower maturity date is early December for plants grown in Waterloo, Iowa.
6. Excellent post-production longevity; flower bracts resist fading.

Plants of the new Poinsettia are most similar to plants of the parent, the cultivar Red Sails. In side-by-side comparisons conducted by the Inventor in Waterloo, Iowa, plants of the new Poinsettia differed from plants of the cultivar Red Sails in the following characteristics:

1. Plants of the new Poinsettia were shorter than plants of the cultivar Red Sails.
2. Plants of the new Poinsettia were more freely branching than plants of the cultivar Red Sails.
3. Plants of the new Poinsettia had more upright lateral branches (narrower branching angle) than plants of the cultivar Red Sails.
4. Plants of the new Poinsettia had smaller and thicker leaves than plants of the cultivar Red Sails.
5. Plants of the new Poinsettia flowered about one week later than plants of the cultivar Red Sails.
6. Plants of the new Poinsettia had smaller inflorescences than plants of the cultivar Red Sails.
7. Flower bracts of plants of the new Poinsettia were more upright than flower bracts of plants of the cultivar Red Sails.
8. Plants of the new Poinsettia had longer postproduction longevity than plants of the cultivar Red Sails as flower bracts of plants of the new Poinsettia did not fade with development whereas flower bracts of plants of the cultivar Red Sails faded with development.

Plants of the new Poinsettia can also be compared to plants of the cultivar Orion, not patented. In side-by-side comparisons conducted by the Inventor in Waterloo, Iowa, plants of the new Poinsettia differed from plants of the cultivar Orion in the following characteristics:

1. Plants of the new Poinsettia were more freely branching than plants of the cultivar Orion.
2. Plants of the new Poinsettia had more upright lateral branches (narrower branching angle) than plants of the cultivar Orion.
3. Plants of the new Poinsettia had smaller, thicker and lighter green-colored leaves than plants of the cultivar Orion.
4. Plants of the new Poinsettia had lighter red-colored flower bracts than plants of the cultivar Orion.
5. Plants of the new Poinsettia flowered about two weeks later than plants of the cultivar Orion.

6. Plants of the new Poinsettia had longer postproduction longevity than plants of the cultivar Orion.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a top perspective view of a typical flowering plant of 'Ted's Red' grown in a container.

The photograph at the bottom of the sheet comprises a close-up view of a typical inflorescence of 'Ted's Red'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Waterloo, Iowa during the autumn and winter under commercial practice in a polyethylene-covered greenhouse with day temperatures about 65 to 70° F. and night temperatures about 65° F. Single plants were grown in 15-cm pots and pinched once. Plants were flowered under natural season short day/long night conditions. Plants were about 18 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Ted's Red.

Parentage: Naturally-occurring branch mutation of *Euphorbia pulcherrima* Willd. cultivar Red Sails, disclosed in U.S. Plant Pat. No. 6,980.

Propagation:

*Type cutting.*—Terminal cuttings.

*Time to initiate roots.*—About 14 to 18 days at 72° F.

*Time to develop roots.*—About 28 days at 72° F.

*Root description.*—Thick, fibrous and freely-branching.

Plant description:

*Plant form.*—Inverted triangle; top of plant mounded.

*Growth habit.*—Compact, upright and uniform plant habit. Narrow branching angle that reduces stem breakage.

*Plant height.*—About 34 to 36 cm.

*Plant diameter or spread.*—About 31 to 32.5 cm.

*Lateral branch description.*—Quantity: About eight lateral branches develop after pinching. Length: About 26 cm. Diameter: About 5 mm. Internode length: About 2.5 cm. Strength: Strong. Texture: Smooth; glabrous. Color: Close to 146A.

*Foliage description.*—Arrangement: Alternate, single. Quantity of leaves per lateral branch: About ten. Length: About 10.5 cm. Width: About 9 cm. Shape: Elliptic. Apex: Acuminate. Base: Obtuse. Margin: Entire with irregular lobing. Venation pattern: Pinnate. Texture, upper and lower surfaces: Glabrous. Surface: Slightly rugose. Aspect: Mostly flat. Orientation: Mostly horizontal.

*Color.*—Developing and fully expanded foliage, upper surface: Close to 147A. Developing and fully expanded foliage, lower surface: Close to 137B. Venation, upper surface: Close to 147B. Venation, lower surface: Close to 137C.

*Petiole.*—Length: About 3 cm. Diameter: About 3 mm. Texture, upper and lower surfaces: Smooth; glabrous. Color: Close to 146A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Relatively late flowering; natural season flower maturity date is early December for plants grown in Waterloo, Iowa.

*Post-production longevity.*—Plants of the new Poinsettia maintain good substance and bract color for about twelve weeks in the greenhouse and about eight weeks under interior conditions.

*Inflorescence size.*—Diameter: About 10.3 to 12.8 cm.

*Flower bracts.*—Quantity per inflorescence: About 18. Shape: Elliptic. Apex: Acuminate. Base: Obtuse. Margin: Entire with irregular lobing. Texture, upper and lower surfaces: Glabrous; velvety. Surface: Mostly smooth. Aspect: Mostly flat. Orientation: Upright. Venation pattern: Pinnate. Color, upper surface: Close to 45A to 45B; color does not fade with development. Color, lower surface: Close to 45B to 45C. Color, venation, upper and lower surfaces: Similar to flower bract color. Bract petiole: Length: About 3 cm. Diameter: About 3 mm. Texture, upper and lower surfaces: Smooth; glabrous. Color: Close to 146A.

*Cyathia.*—Quantity per corymb: About 13. Diameter of cyathia cluster: About 2 by 2.5 cm. Shape: Ovoid. Color, immature: 144B. Color, mature: 144A.

*Peduncle.*—Length: About 4 mm. Diameter: About 2 mm. Strength: Strong. Aspect: Upright. Texture: Smooth; glabrous. Color: 144A.

*Stamens.*—Quantity per cyathium: About ten. Anther shape: Oval. Anther length: Less than 1 mm. Anther color: Close to 12A. Amount of pollen: Scarce. Pollen color: Close to 12A.

*Pistils.*—None observed.

*Nectaries.*—Quantity per cyathium: About one or two. Size: About 2 mm by 3 mm. Color: Close to 14A.

Disease/pest resistance: Plants of the new Poinsettias have been observed to be resistant to Pythium, Crown Rot and whiteflies.

It is claimed:

1. A new and distinct cultivar of Poinsettia plant named 'Ted's Red', as illustrated and described.

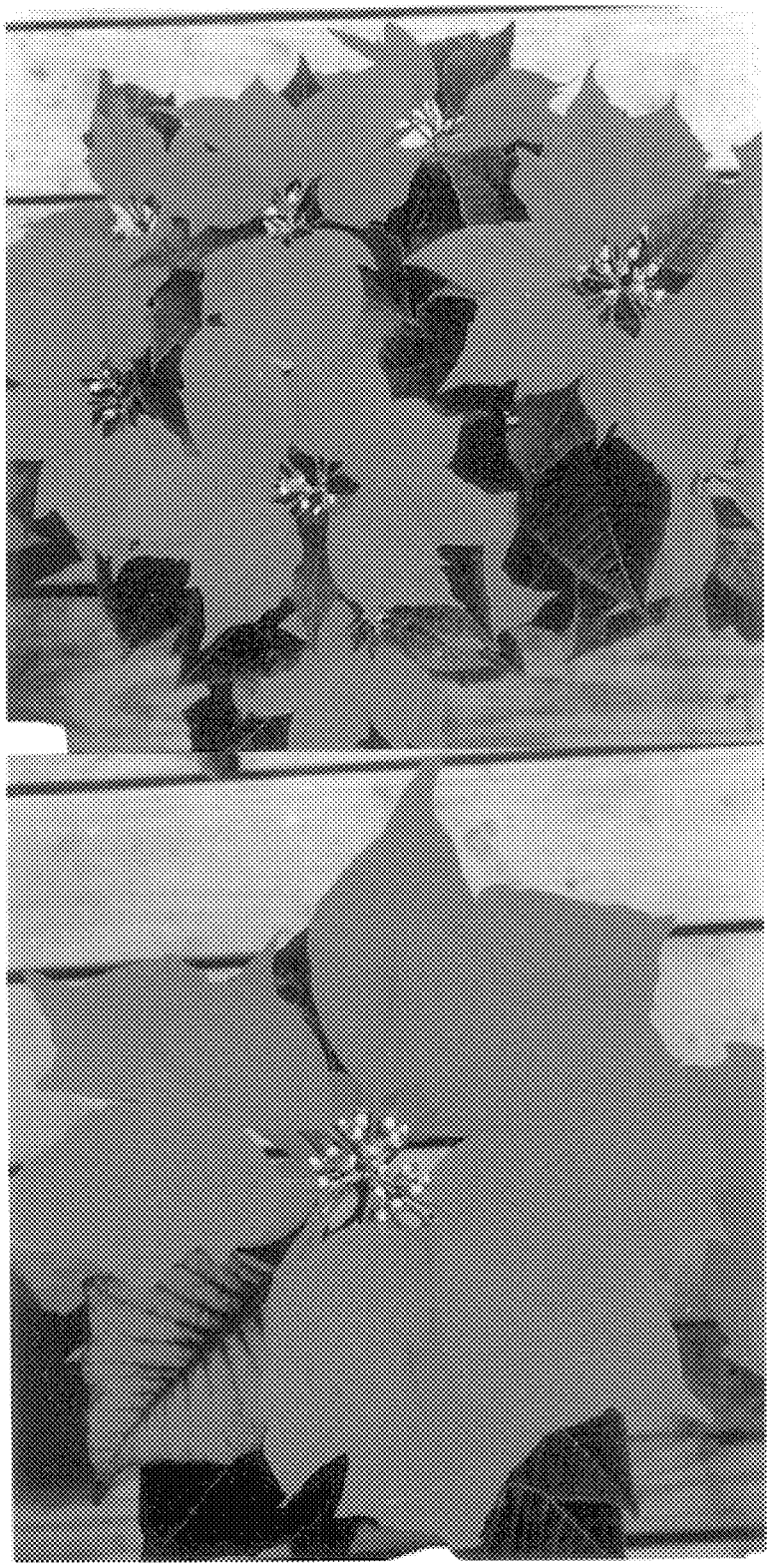

* * * * *